(12) United States Patent
Jordan et al.

(10) Patent No.: US 8,460,305 B2
(45) Date of Patent: Jun. 11, 2013

(54) CANNULATED SURGICAL SCREW BONE FILLER ADAPTER

(76) Inventors: Christopher S. Jordan, Midwest City, OK (US); Rose Wolf, Kodiak, AL (US)

( * ) Notice: Subject to any disclaimer, the term of this patent is extended or adjusted under 35 U.S.C. 154(b) by 696 days.

(21) Appl. No.: 12/658,345

(22) Filed: Feb. 5, 2010

(65) Prior Publication Data
US 2010/0298887 A1  Nov. 25, 2010

Related U.S. Application Data

(63) Continuation-in-part of application No. 12/454,696, filed on May 21, 2009, now Pat. No. 8,231,632.

(51) Int. Cl.
*A61B 17/58* (2006.01)

(52) U.S. Cl.
USPC ........................................................... 606/92

(58) Field of Classification Search
USPC ................ 606/304, 323, 92–95, 53, 300, 301
See application file for complete search history.

(56) References Cited

U.S. PATENT DOCUMENTS

| 7,354,442 | B2 * | 4/2008 | Sasso et al. .................... 606/280 |
| 7,371,241 | B2 * | 5/2008 | Evans et al. ...................... 606/92 |
| 2006/0122625 | A1 | 6/2006 | Truckai |
| 2007/0032567 | A1 | 2/2007 | Beyar |
| 2007/0038221 | A1 * | 2/2007 | Fine et al. ......................... 606/73 |
| 2007/0055257 | A1 | 3/2007 | Vaccaro |
| 2007/0270876 | A1 * | 11/2007 | Kuo et al. ........................ 606/92 |
| 2008/0195114 | A1 * | 8/2008 | Murphy .......................... 606/94 |
| 2009/0054934 | A1 | 2/2009 | Beyar |

* cited by examiner

Primary Examiner — Kevin T Truong
Assistant Examiner — Michael Araj

(57) ABSTRACT

An adapter attached between a dispenser containing a bone void filler and the head of a cannulated surgical screw allows the cannulated surgical screw to be used as a port to inject bone void filler into a bone void during the course of a surgical repair which would use a surgical screw to attach broken or separated bone fragments providing a more secure bone anchor matrix within which the surgical screw is set.

4 Claims, 5 Drawing Sheets

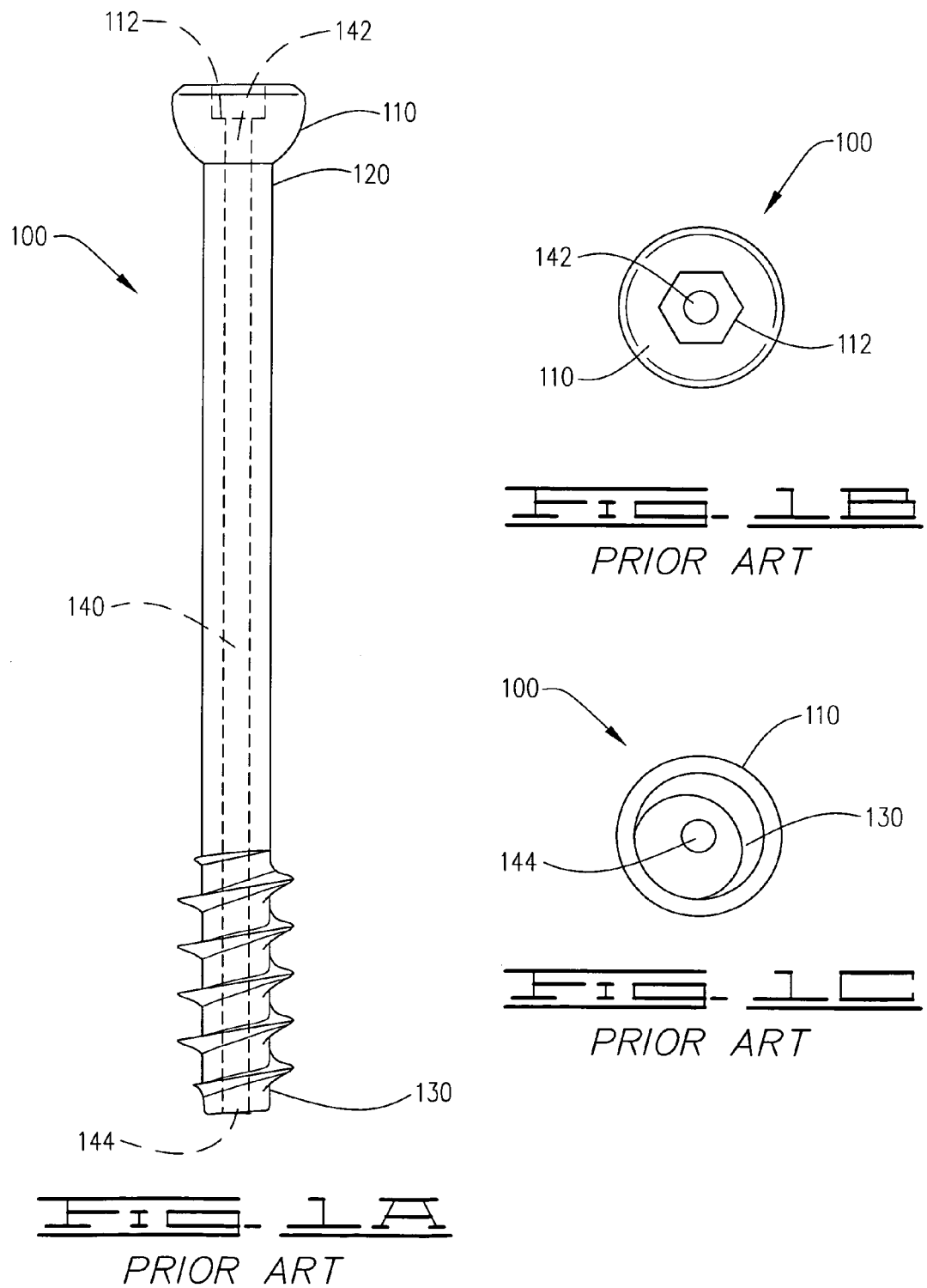

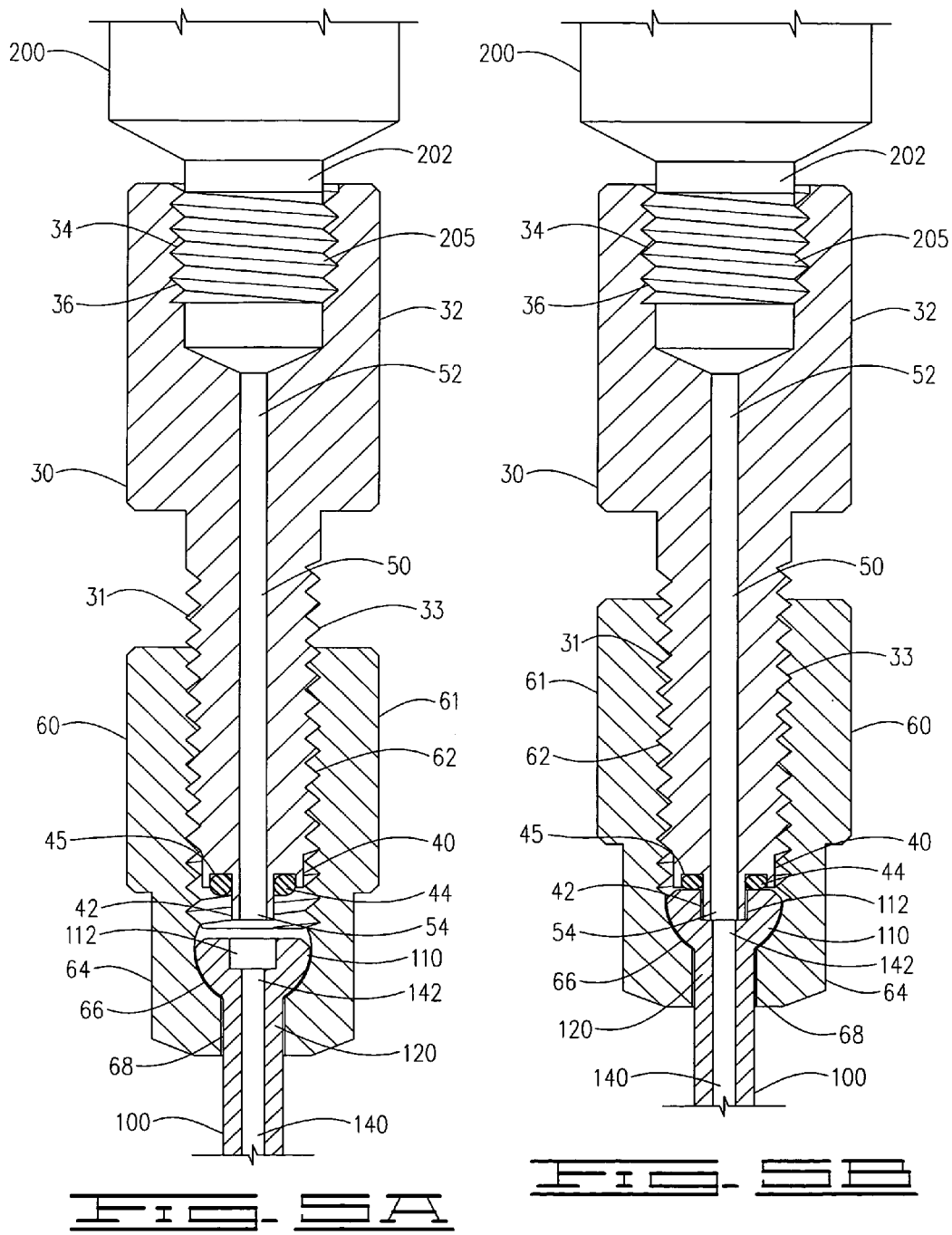

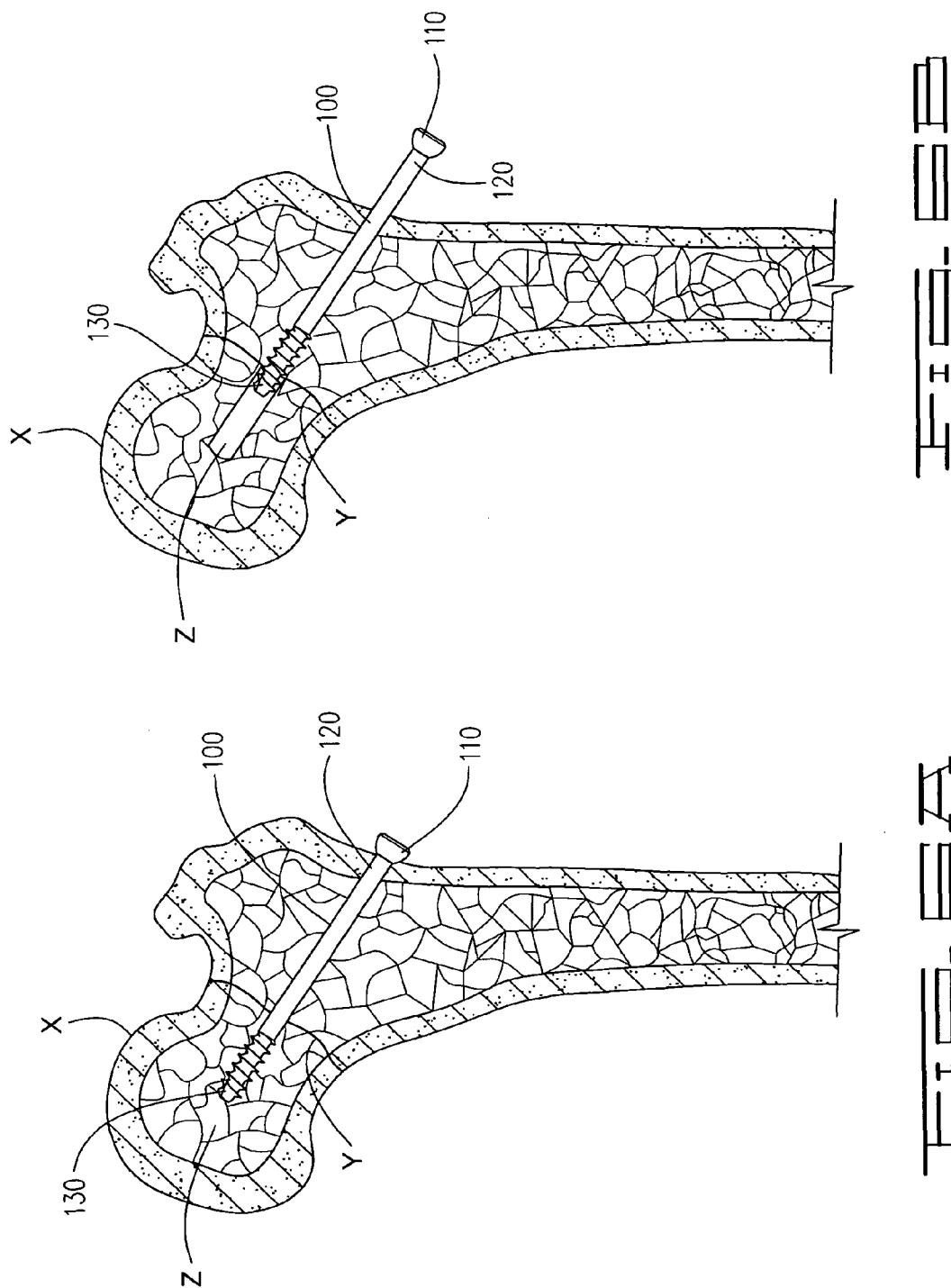

CANNULATED SURGICAL SCREW BONE FILLER ADAPTER

CROSS REFERENCE TO RELATED APPLICATIONS

This is a Continuation-in-Part Application of U.S. patent application Ser. No. 12/454,696, filed by the same inventors on May 21, 2009, now U.S. Pat. No. 8,231,632 with additional reference made to U.S. patent application Ser. No. 12/456,577 filed on Jun. 18, 2009 by the same inventors.

I. BACKGROUND OF THE INVENTION

1. Field of Invention

An adapter attached between a syringe containing a bone void filler and the head of a cannulated surgical screw allows the cannulated surgical screw to be used as a port to inject bone void filler into a bone void during the course of a surgical repair which would use a surgical screw to attach broken or separated bone fragments providing a more secure bone anchor matrix within which the surgical screw is set.

2. Description of Prior Art

A preliminary review of prior art patents was conducted by the applicant which reveal no prior art patents in a similar field or having similar use in the field of orthopedic surgery. The disclosed prior art inventions do not disclose the same or similar elements as the present cannulated screw bone filler adapter, nor do they present the material components in a manner contemplated or anticipated in the prior art.

Bone cements are known in the art of orthopedic surgery and have been discussed in articles including *The use of Calcium Phosphate Bone Cement in fracture Treatment*, Bajammal, Sohail S., et al., Journal of Bone and Joint Surgery, Volume 90, pgs. 1186-1196, and articles referenced therein and in U.S. Patent Application No. 2007/0032567 to Beyar. Methods of injection of a bone filler are disclosed in U.S. Patent Application No. 2009/0054934, to Beyar, which provide methods for accessing a void in the bone, introduction of bone cement into a void, introduction of an expandable filler into the void, expanding the filler and allowing the cement to set. This application clearly points out a danger in contamination of non-intentional tissue surrounding the fracture site with the bone cement by leakage or by overfill causing further damage to the affected bone being repaired and also by introduction of the bone cement through mistake or accident. Other methods employing the use of a surgical procedure known as Kyphoplasty, wherein a balloon is inflated within a bone void with the balloon further filled with a bone filler material to minimize collateral exposure to the bone cement, is demonstrated in U.S. Patent Application No. 2006/0122625 to Truckai.

Another patent application, U.S. patent Application No 2007/0055257 to Vaccaro, has attempted to utilize modified cannulated screws to accomplish an injection of a syringe containing a bone filler, the head of the cannulated screw having an externally threaded inner head adapted to a syringe having an internally threaded collar with an injector tip which enters the longitudinal central bore in the cannulated screw, the cannulated screw having a side discharge port to release the bone filler injected into the central bore.

The present adapter utilizes a typical prior art cannulated surgical screw as shown in FIGS. 1A-1C, available from surgical supply companies including MIKROMED, DEPUY®, OSTEOMED® and SYNTHES®. The adapted secures to the head of the cannulated screw by screwing the two threaded components together, locking the adapter to the head of the cannulated screw. A pre-filled bone filler syringe having a course outer thread which would normally be adapted to receive an internally threaded head portion of a hollow needle would then be attached to an internally threaded head cap of the upper component of the adapter, after which the bone filler contained within syringe may be injected through the adapter and the longitudinal central bore of the cannulated screw through the tip of the cannulated screw into a bone void below the tip of the cannulated screw which will secure the tip of the cannulated screw into the bone void filler cement subsequent to the hardening of the cement. Anchoring the tip of the surgical screw would reduce the chance of the screw backing out of the bone, which is not an uncommon occurrence, in the same manner that filling a post hole with cement to anchor a fencepost stabilizes and supports the fencepost over simply ramming the fencepost into the dirt.

II. SUMMARY OF THE INVENTION

A most common fracture of a bone occurs when the head of the bone, most commonly a femur, humerus, radius, or tibia, is broken from the remainder of the bone. This repair is a difficult repair and ordinarily requires a surgical intervention. A most common repair involves the insertion of one or more screws to attach the broken end of the bone to the remainder of the bone through use of surgical screws. These screws are placed in the bone either to hold bone to bone or to hold the bone together by use of a bracket or brace attached to the fixed portion of the bone and also attaching the broken portion of the bone, most commonly the head, to the bracket to allow the aligned bones to grow together again.

Take for example a situation where the neck of the femur is fractured. This is not uncommon, especially in the elderly or those involved in traumatic associated injuries. The fracture occurs along the neck and thus the head of the femur must be joined to the upper end of the femur through the trochanter. Once aligned, a pathway is drilled from the lateral side of the femur below the greater trochanter, through the neck of the femur and into the inner cavity of the head of the femur. Inside the head of the femur is a space which is filled with a very porous bone material, but much less dense than the bone itself. As a person get older, this inner portion of the head becomes more porous and eventually creates a large void or extremely porous space within the head. This poses a fixation problem for the placement and secure anchoring of a surgical screw inserted within the drilled pathway. Thus, several screws must be used to make a secure attachment of the head to the femur unless something could be done to fill the bone void or very porous space with some material strong enough to provide an anchoring matrix to further secure the tip of the surgical screw into the bone to prevent it from becoming loose or being backed out over time.

It is known in the art that use of bone cement is a material with a history of success in bone to bone connection, delivered in a paste or liquid and hardening into a solid biocompatible material. Surgical success has been demonstrated by statistical comparison. Companies provide this bone cement in solid materials which are reduced to a paste or liquid prior to use, or deliver bone cements in pre-filled syringes. Prior art has demonstrated use of bone cements applied externally to the surface of a bone, or injected into space around or below a vertebrae in a process known as Kyphoplasty to repair fractured vertebrae by elevating the vertebrae to a normal position and then injecting a balloon used to lift the vertebrae with the bone cement to hold and retain the vertebrae in the elevated position caused by the balloon. Injection of the bone cement is through a tube inserted through the back and into the inflated balloon during the surgical procedure, which last about an hour for each vertebrae, takes about a day to recover and instantly provides a permanent relief from pain caused by vertebral compression. However, this process has not been used in the past for repair or reduction of the reattachment of the end of a bone using surgical screws. There is some discussion of a modified cannulated screw used in repair of a vertebrae to provide access through the cannulated screw during surgery by providing a side access through the screw for a spinal rod or other surgical tool after placement of the screw.

Currently there is no technique or procedure disclosing the use of a cannulated screw as a delivery means for the injection of a liquid or gel into a bone void. There is no disclosed procedure for filling a bone void through injection. There is no mention in any prior art of an adapter which is located between a syringe and a cannulated surgical screw to prevent spillage or contamination of surrounding tissue with bone cement which seals a delivery passage between the end of a syringe and the head of a cannulated surgical screw. There is also no disclosed method or apparatus to inject a bone void with bone cement to secure a surgical screw within the bone. Thus, the disclosed adapter is in no way mentioned in prior art, the procedure for the use of the disclosed adapter is not revealed in prior art and thus not anticipated nor contemplated in any prior art. No method or device is disclosed in any prior art to address the issue of providing a more secure anchor within a bone void for a surgical screw, cannulated or other, so it is unlikely that any prior art patent would be designed or adapted to a similar use to resolve a similar issue.

Filling a bone void to provide a more stable anchoring matrix would provide a more secure anchoring of a surgical screw, requiring fewer screws and providing a better fixation of the bone repair. As a screw is already being used for this procedure, providing the screw as an already available cannulated surgical screw would require no additional surgical procedure than already being done. The cannulated screw, having already been inserted into a drilled location through the bone, is already located with the tip of the surgical screw in the area where the bone void is presented, already places the tip of the surgical screw in an perfect location for the placement of a bone filler cement within the bone void of the bone being repaired. We are simply employing the cannulated surgical screw as a port for the injection of bone cement through the longitudinal channel directed to the tip of the surgical screw, after having fully inserted the surgical screw into the bone and then partially backed it out for the injection of the bone void cement into the bone void through the cannulated surgical screw, and then reinserting the surgical screw to its full insertion.

The disclosed adapter provides a secure connection between a cannulated surgical screw and a syringe filled with a bone filler cement to deliver the bone filler cement into a bone void for a secure attachment of a fully inserted surgical screw into a bone. The disclosed adapter is installed upon the head of the cannulated surgical screw without requiring a hand to hold the adapter on the screw head during application of the syringe to the opposing end of the adapter. The disclosed adapter can be used with existing and available surgical appliances and during an existing and currently used surgical procedure to inject bone filler cement into a directed bone without contamination of the surgical tissue with the bone filler cement.

III. DESCRIPTION OF THE DRAWINGS

The following drawings are submitted with this utility patent application.

FIG. 1A is a side view of a prior art cannulated surgical screw.

FIG. 1B is a top view of the prior art cannulated surgical screw.

FIG. 1C is a bottom view of the prior art cannulated surgical screw.

FIG. 5A is a side cross sectional view of the bone filler dispenser, the cannulated screw bone filler adapter and a cannulated surgical screw with the top member and the bottom member of the cannulated screw bone filler adapter positioning the cylindrical tip of the upper member into the upper end of the longitudinal bore of the cannulated surgical screw prior to being fully secured for injection of the bone filler into the central channel.

FIG. 5B is a side cross sectional view of the bone filler dispenser, the cannulated screw bone filler adapter and a cannulated surgical screw with the upper member and the lower member fully secured, placing the cylindrical tip of the upper member into the into the upper portion of the longitudinal bore of the cannulated surgical screw, with the O-ring being compressed forming a seal, for injection of the bone filler through the longitudinal bore and eventually out of the lower end of the longitudinal bore.

FIG. 6A is a cross sectional view of the fractured head of a femur indicating a full insertion of a cannulated surgical screw to secure the fracture site.

FIG. 6B is a cross sectional view of the fractured head of a femur indicating a backout position of the cannulated surgical screw as shown in FIG. 6A, positioning the cannulated surgical screw in the proper position for application of the cannulated screw bone filler adapter and the bone filler dispenser for insertion of bone filler cement into the bone void within the fractured head of the femur.

IV. DESCRIPTION OF THE PREFERRED EMBODIMENT

Figure 2A:
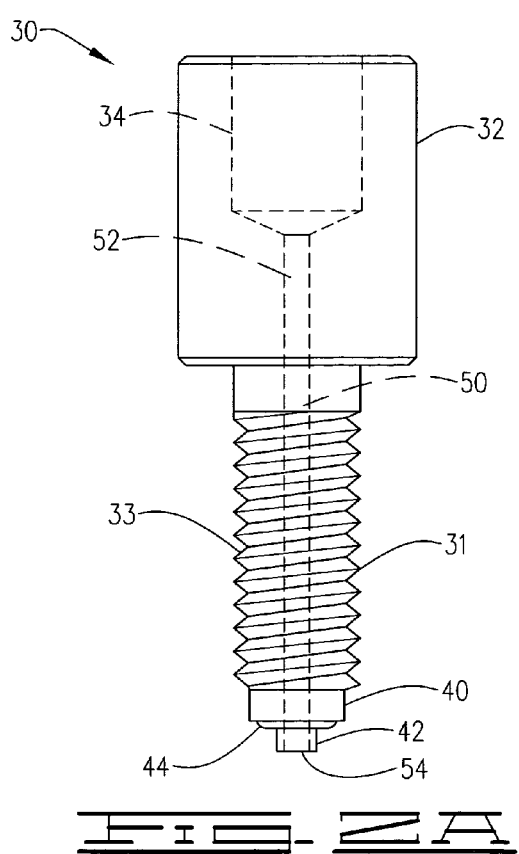
FIG. 2A is a side view of the upper member of a cannulated screw bone filler adapter.
Figure 2B:
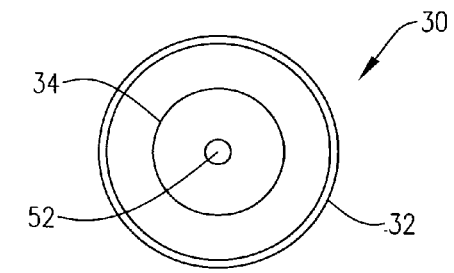
FIG. 2B is a top view of the upper member of the cannulated screw bone filler adapter.
Figure 2C:
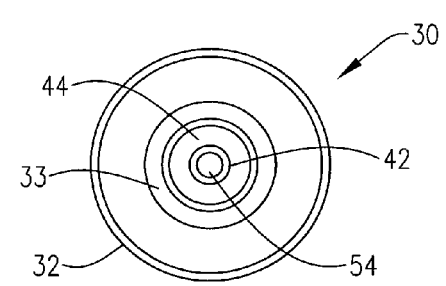
FIG. 2C is a bottom view of the upper member of the cannulated screw bone filler adapter.
Figure 3B:
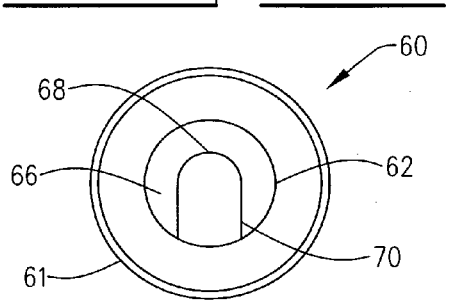
FIG. 3B is a top view of the lower member of the cannulated screw bone filler adapter.
Figure 3A:
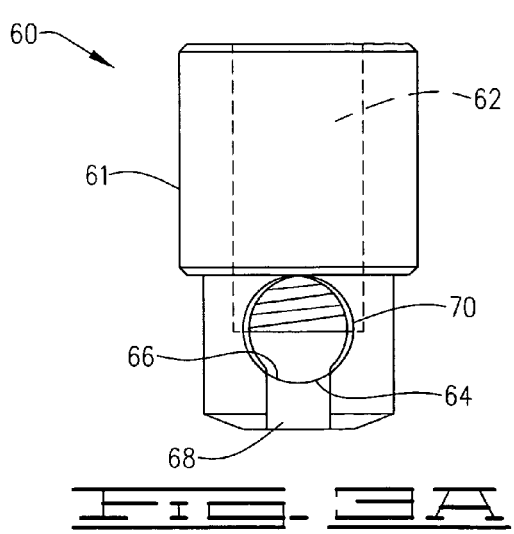
FIG. 3A is a side view of a lower member of the cannulated screw bone filler adapter.
Figure 3C:
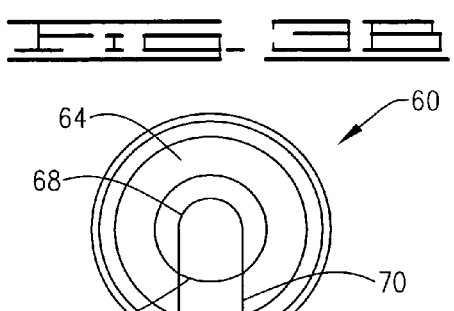
FIG. 3C is a bottom view of the lower member of the cannulated screw bone filler adapter.
Figure 4:
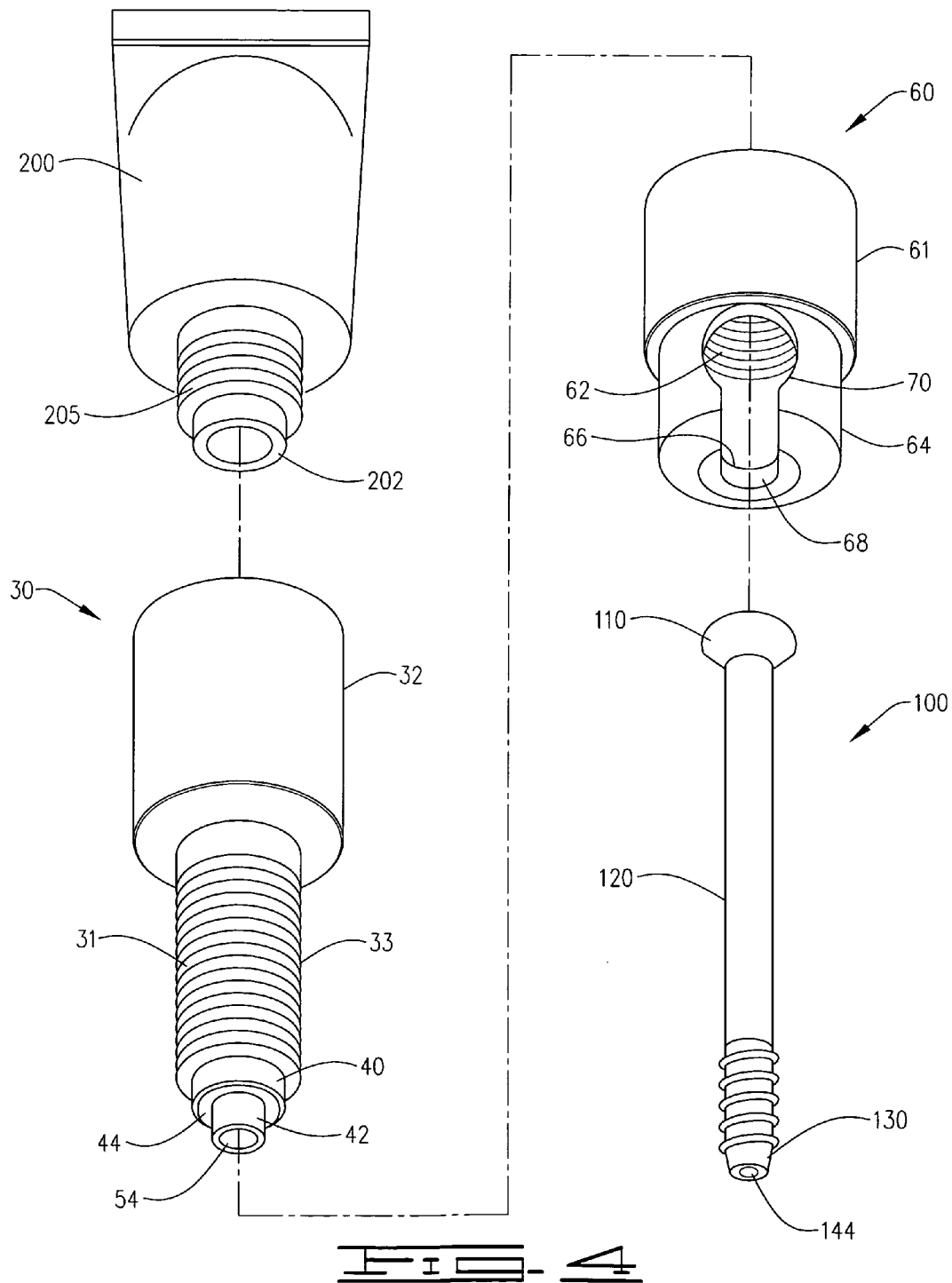
FIG. 4 is an exploded view of a bone filler dispenser, the upper and lower members of the cannulated screw bone filler adapter and a prior art cannulated surgical screw.

An adapter 10 providing a secure connection between a head 110 of an externally threaded cannulated surgical screw 100, indicated in FIGS. 1A-C, 4 and 5A-B, defining the head 110, neck 120 and tip 130, and a bone filler dispenser 200, FIGS. 4 and 5A-B, filled with a bone filler cement, to inject a bone filler cement through an upper end 142 of a longitudinal bore 140 in the cannulated surgical screw 100 through a lower end 144 of the longitudinal bore 140 into a bone void z within a bone x undergoing a surgical repair at a fracture site y, FIGS. 6A-B, the adapter 10 providing an upper member 30, FIGS. 2A-C, and a lower member 60, FIGS. 3A-C, the upper member 30 providing an external lateral thread 31 upon an elongated shaft 33, an expanded upper dispenser receiving collar 32, a lower nipple 40 and a central bore 50 from the upper dispenser receiving collar 32 to the nipple 40, and the lower member 60 defining an expanded upper portion 61 providing an internal threaded inner cavity 62 receiving the external lateral threads 31 of the elongated shaft 33 of the upper member 30, a bottom portion 64 defining a contoured head cradle 66, and a lower circular screw neck support 68, and providing a lateral cannulated screw insertion port 70. The upper member 30 further defines the upper dispenser receiving collar 32 defining an inner cylindrical chamber 34 within which an upper end 52 of the central bore 50 is provided, the inner cylindrical chamber 34 having a course internal thread 36 to accept and retain a course external thread 205 of a lower end 202 of the dispenser 200, where the dispenser 200 is provided with such course external threads 205, preferred to securely connect the upper dispenser receiving collar 32 to the lower end 202 of the dispenser 200 to prevent spillage of the bone void cement during pressurized transfer of the bone cement. The nipple 40 further defines a cylindrical tip 42 and an O-ring seat 45 within which is placed a deformable O-ring seal 44, the cylindrical tip containing a lower end 54 of the central bore 50, the O-ring 44 compressibly deforming to create a seal between the lower nipple 40 upon the head 110 of the cannulated surgical screw 100, FIG. 1B, the cylindrical tip 42 being secured within the upper end 52 of the longitudinal bore 50 and around the tool depression 112 within the head 110 of the cannulated screw 100 to prevent spillage or leakage of the bone filler cement during injection under pressure from the dispenser 200, through the adapter 10 and into the longitudinal bore 140 of the cannulated surgical screw 100.

The assembly and relationship of the adapter 10, the dispenser 200 and the cannulated surgical screw 100 is demonstrated in FIG. 4, with the lower end 202 of the dispenser 200 engaging the inner cylindrical chamber 34 of the upper dispenser receiving collar 32 of the upper member 30, the upper member 30 is threadably engaged with the lower member 60 and the lower member 60 retains the head 110 of the inserted cannulated surgical screw 100, with the lower nipple 40 inserted into the head 110 of the cannulated surgical screw 100, with the upper tool seat 44 within the tool depression 112 of the head 110 of the cannulated surgical screw 100 and the cylindrical tip 42 placed within an upper end 142 of the longitudinal bore 140 in the cannulated surgical screw 100, thus providing a closed channel between the lower end 202 of the dispenser 200 and the longitudinal bore 140 of the cannulated surgical screw 100 all the way through to the lower end 144 of the longitudinal bore 140 at the tip 130 of the cannulated surgical screw 100, FIG. 1C.

Use and application of the adapter during a surgical procedure to repair a fracture site y of a bone x would occur after a subject bone x is drilled, reduced and subsequent to a full insertion of the cannulated surgical screw 100 penetrating into a bone void z to secure and fix the fractured site y of a bone, as indicated in FIG. 6A. The cannulated surgical screw 100 is then partially rotated back out, as indicated in FIG. 6B. The lower member 60 is then placed over the head 110 of the cannulated surgical screw 100 by sliding the head 110 of the cannulated surgical screw 100 through the lateral cannulated screw insertion port 70, seating the head 110 of the cannulated surgical screw 100 within the contoured head cradle 66 of the lower member 60 with the neck 120 of the cannulated surgical screw 100 extending through the circular screw neck support 68. The upper member 30 is then threadably inserted into the lower member 60 until the cylindrical tip 42 is within the upper end 142 of the longitudinal bore 140 of the cannulated surgical screw 100 and until the cylindrical tip 42 is secured within the upper end 52 of the longitudinal bore 50 in the head 110 of the cannulated surgical screw 100, with the O-ring 44 being compressed against the head 110 of the cannulated screw around the tool depression 112 to prevent any leakage of bone filler cement during injection of the bone filler cement. The lower end 202 of the dispenser 200 is then inserted and connected to the inner cylindrical chamber 34 of the upper dispenser receiving collar 32. Once secured, the bone filler cement may be deported through the central bore 50 of the upper member 30, through the longitudinal bore 140 and into the bone void within the subject bone x to fill the bone void with bone filler cement. The dispenser 200 would then be detached from the upper member 30, the upper member 30 separated from the lower member 60, and the head 110 of the cannulated surgical screw 100 released from the lower member 60 by sliding the lower member 60 away from the head 110 of the cannulated surgical screw 100. After ensuring that no residual bone filler cement is present on the head 110 of the cannulated surgical screw 100, the cannulated surgical screw 100 would then be reinserted fully into the bone x, with the tip 130 of the cannulated surgical screw 100 being set within the bone filler cement which would set to a hard matrix within the bone void z. The method disclosed utilizing the adapter would be identical to the method patent previously filed by the same inventors as reference herein.

The disclosed adapter provides a secure connection between a cannulated surgical screw and a dispenser filled with a bone filler cement to deliver the bone filler cement into a bone void for a secure attachment of the tip of a fully inserted surgical screw into a bone. The disclosed adapter is installed upon the head of the cannulated surgical screw without requiring a hand to hold the adapter on the screw head during application of the dispenser to the opposing end of the adapter. The disclosed adapter can be used with existing and available surgical appliances and during an existing and currently used surgical procedure to inject bone filler cement into a directed bone without contamination of the surgical tissue with the bone filler cement. While the invention has been particularly shown and described with reference to a preferred embodiment thereof, it will be understood by those skilled in the art that changes in form and detail may be made therein without departing from the spirit and scope of the invention.

What is claimed is:

1. A cannulated surgical screw adapter, providing a secure connection between a head of an externally threaded cannulated surgical screw and a dispenser filled with a bone filler cement, to inject the bone filler cement through a longitudinal bore in said cannulated surgical screw into a bone void within a bone undergoing a surgical repair, said adapter comprising:

an upper member defining an expanded upper dispenser receiving collar defining an inner threaded cylindrical chamber, an external lateral thread upon an elongated shaft, a lower nipple extending from said elongated shaft further defining a cylindrical tip and a central bore from said inner threaded cylindrical chamber through said cylindrical tip, and a lower member defining an expanded upper portion and having an internal threaded inner cavity receiving said external lateral threads of said elongated shaft of said upper member, and a lower portion defining an inner contoured head cradle, a lower circular screw neck support, and a lateral cannulated screw insertion port, wherein a lower end of said dispenser is secured within said inner threaded cylindrical chamber of said upper dispenser receiving collar while said head of said cannulated surgical screw is inserted through said lateral cannulated screw insertion port into said contoured head cradle, said elongated shaft of said upper member further inserted into said internal threaded inner cavity of said lower member until said cylindrical tip is secured within said longitudinal bore of said cannulated surgical screw to inject said bone filler cement into said longitudinal bore into the bone void within which said cannulated surgical screw has been installed.

2. The adapter, as disclosed in claim 1, further comprising:
said upper dispenser receiving collar defining said inner cylindrical chamber within which an upper end of said central bore is presented, said inner cylindrical chamber having a course internal thread accepting and retaining a course external thread of a lower end of said dispenser, securely connecting said upper dispenser receiving collar to said lower end of said dispenser to prevent spillage of the bone void cement during pressurized transfer of the bone cement.

3. The adapter, as disclosed in claim 1, further comprising:
said nipple defining said cylindrical tip within which a lower end of said central bore is presented, said nipple further defining an O-ring seat containing a compressible O-ring seal surrounding said cylindrical tip, said cylindrical tip being inserted within an upper end of said longitudinal bore within a tool depression in said head of said cannulated surgical screw, said O-ring seal, when pressed against said head of said cannulated screw forming a seal to prevent spillage or leakage of the bone filler cement during injection under pressure from said dispenser, through said central bore in said upper member, and into a lower end of said longitudinal bore of said cannulated surgical screw.

4. The adapter, as disclosed in claim 1, further comprising:
said upper dispenser receiving collar defining said inner cylindrical chamber within which an upper end of said central bore is presented, said inner cylindrical chamber having a course internal thread accepting and retaining a course external thread of a lower end of said dispenser, securely connecting said upper dispenser receiving collar to said lower end of said dispenser to prevent spillage of the bone void cement during pressurized transfer of the bone cement; and
said nipple defining said cylindrical tip within which a lower end of said central bore is presented, said nipple further defining an O-ring seat containing a compressible O-ring seal surrounding said cylindrical tip, said cylindrical tip being inserted within an upper end of said longitudinal bore within a tool depression in said head of said cannulated surgical screw, said O-ring seal, when pressed against said head of said cannulated screw forming a seal to prevent spillage or leakage of the bone filler cement during injection under pressure from said dispenser, through said central bore in said upper member, and into a lower end of said longitudinal bore of said cannulated surgical screw.

* * * * *